United States Patent
Plumeré et al.

(10) Patent No.: US 12,098,413 B2
(45) Date of Patent: Sep. 24, 2024

(54) METHOD FOR REMOVING DISSOLVED OXYGEN, USED IN AN ELECTROCHEMICAL BIOSENSOR THAT USES AN OXIDASE AS THE SENSOR ENZYME

(71) Applicant: RUHR-UNIVERISTAT BOCHUM, Bochum (DE)

(72) Inventors: Nicolas Plumeré, Bochum (DE); Huijie Frau Zhang, Bochum (DE); Adrian Ruff, Grosselfingen (DE); Tobias Vöpel, Dortmund (DE)

(73) Assignee: RUHR-UNIVERISTAT BOCHUM, Bochum (DE)

( * ) Notice: Subject to any disclaimer, the term of this patent is extended or adjusted under 35 U.S.C. 154(b) by 806 days.

(21) Appl. No.: 17/251,299

(22) PCT Filed: Jun. 13, 2019

(86) PCT No.: PCT/EP2019/065607
§ 371 (c)(1),
(2) Date: Dec. 11, 2020

(87) PCT Pub. No.: WO2019/238887
PCT Pub. Date: Dec. 19, 2019

(65) Prior Publication Data
US 2021/0254120 A1    Aug. 19, 2021

(30) Foreign Application Priority Data
Jun. 14, 2018    (DE) .................... 10 2018 209 611.2

(51) Int. Cl.
G01N 27/327    (2006.01)
C12Q 1/00    (2006.01)
C12Q 1/26    (2006.01)
C12Q 1/30    (2006.01)

(52) U.S. Cl.
CPC ............. *C12Q 1/005* (2013.01); *C12Q 1/004* (2013.01); *C12Q 1/26* (2013.01); *C12Q 1/30* (2013.01); *G01N 27/3271* (2013.01); *G01N 27/3276* (2013.01); *G01N 27/3277* (2013.01)

(58) Field of Classification Search
CPC .......... C12Q 1/005; C12Q 1/004; C12Q 1/26; C12Q 1/30; G01N 27/3276; G01N 27/3277; G01N 27/327–3272; G01N 27/3274
See application file for complete search history.

(56) References Cited

U.S. PATENT DOCUMENTS 9,187,779 B2    11/2015    Plumeré et al.
2012/0211372 A1    8/2012    Plumeré et al.

OTHER PUBLICATIONS

International Search Report and Written Opinion, PCT Application No. PCT/EP2019/065607 dated Sep. 26, 2019.
Lopez et at., "A Polymer Multilayer Based Amperometric Biosensor for the Detection of Lactose in the Presence of High Concentrations of Glucose", Electroanalysis, 2017.

(Continued)

Primary Examiner — Alexander S Noguerola
(74) Attorney, Agent, or Firm — The Dobrusin Law Firm, P.C.

(57) ABSTRACT

The present invention relates to a method for removing oxygen, used in an electrochemical biosensor, and to a measurement system and a method for electrochemically determining a concentration of an analyte using said method.

20 Claims, 6 Drawing Sheets

(56) References Cited

OTHER PUBLICATIONS

Pablo et al., "Glucose Amperometric Biosensor Based on the Co-immobilization of Glucose Oxidas (GOx) and Ferrocene in Poly(pyrrole) Generated from Ethanol/Water Mixtures", Journal of the Brazilian Chemical Society, Bd. 12, Nr. 6, Jan. 1, 2001.
Eun-Hyung Yoo et al., "Glucose Biosensors: An Overview of Use in Clinical Practice", Sensors, Bd. 10, Nr. 5, May 4, 2010.
Plumeré et al., "Enzyme-Catalyzed $O_2$ Removal System for Electrochemical Analysis under Ambient Air: Application in an Amperometric Nitrate Biosensor", Analytical Chemistry, 2012, pp. 2141-2146.
International Preliminary Report on Patentability, PCT Application No. PCT/EP2019/065607 dated Dec. 15, 2020.

METHOD FOR REMOVING DISSOLVED OXYGEN, USED IN AN ELECTROCHEMICAL BIOSENSOR THAT USES AN OXIDASE AS THE SENSOR ENZYME

PRIOR ART

The present invention proceeds from a method for determining a concentration of an analyte in a sample. Such methods are known in principle from the prior art and are carried out many millions of times per day. Examples mentionable here are checks in the area of food production and blood glucose measurements. From the latter alone, 24 million procedures are carried out per day in Germany on patients suffering from a diabetes mellitus disease.

To measure a concentration of an analyte, for example a glucose concentration or a lactose concentration, use is usually made of electrochemical biosensors which, with the aid of enzymatic reactions, are suitable for ascertaining the concentrations to be measured. A major challenge in these methods is that oxygen dissolved in the sample influences the measurement results. In the case of electrochemical biosensors, the presence of dissolved oxygen leads to a short circuit of the electron transfer process from the analyte to the electrode. In the case of low concentrations of the analyte, this leads to considerable inaccuracies.

Although the use of tests to ascertain the blood glucose concentration of diabetes patients is highly necessary and can save lives, the methods used are always a subject of dispute because of insufficient accuracy. The glucose biosensors most widespread on the market are based on the enzymes glucose dehydrogenase or glucose oxidase. The two enzymes have different disadvantages that can influence the accuracy of measurement. For instance, some of the glucose dehydrogenase-based systems deliver false measurement values in the presence of certain medicaments and react nonspecifically with other sugars such as maltose, galactose and xylose. This leads to falsely elevated measurement values, which can lead to nondetection of hypoglycemias with fatal consequences.

Test systems based on glucose oxidase are less vulnerable to medicaments, different pH values and the blood temperature of the patient and, owing to their specificity for glucose, not vulnerable to other sugars. Furthermore, glucose oxidase is inexpensive to produce. However, glucose oxidase test systems are sensitive to elevated or lowered oxygen concentrations. For instance, an elevated oxygen concentration leads to lower measurement values, whereas a lowered oxygen concentration results in excessive measurement values. Furthermore, the formation of hydrogen peroxide, which can deactivate the glucose oxidase used, occurs in the presence of oxygen.

From the prior art, methods for oxygen removal are known, in which glucose oxidase, galactose oxidase or pyranose oxidase were combined with catalase (U.S. Pat. No. 9,187,779B2). The two enzymes allow the removal of oxygen. In this process, the oxidase catalyzes the oxidation of a sugar (glucose, galactose) to form a hemiacetal (glucose oxidase), ketone (pyranose oxidase) or aldehyde (galactose oxidase) and hydrogen peroxide. The resultant hydrogen peroxide is degraded by the added catalase to form oxygen and water. This combination allows the effective removal of oxygen in the presence of the corresponding sugars. However, this system cannot be used for the development of a biosensor for detecting glucose, since the oxidoreductases used (apart from galactose oxidase) are specific for glucose.

A degradation of glucose would, however, distort the measurement result of a glucose biosensor. A further disadvantage of the described method is that the oxidoreductases used (glucose oxidase, galactose oxidase and pyranose oxidase) can also transfer the electrons to a mediator of the measurement process, and this would lead to distortion of the measurement results.

The prior art further includes a method in which an oxidase for removing oxygen was used in an oxidase-based electrochemical sensor system. In this case, a spatial the separation of the two processes (02 removal and detection of the analyte) is made ("A Polymer Multilayer Based Amperometric Biosensor for the Detection of Lactose in the Presence of High Concentrations of Glucose" by F. Lopez et al., "Electroanalysis" 2017). In this case, the spatial separation is realized by the use of multiple layers. A lower layer is electrically connected to an electrode and can transfer electrons. Present in said layer is an enzyme specific for the analyte. Applied to the lower layer is an upper layer in which enzymes for removing oxygen or other molecules such as, for example, glucose and hydrogen peroxide are embedded. However, this structure has the disadvantage that the sensor enzyme is located in the lower layer. Owing to said structure, diffusion processes can limit the concentration of the analyte in the lower layer, and the application of the upper layer can impair the activity of the enzymes in the lower layer.

Furthermore, methods for oxygen removal using alcohol oxidase are already known from the prior art. In this case, the alcohol oxidase is produced in bacteria or fungi. These cells are then used as a whole, as cell lysate or as cell extract for removing oxygen. In the case of this use, the cells or extracts are packed into an oxygen-permeable membrane. However, the use of cells or cell extracts is not practical for the development of a biosensor, since they are difficult to integrate in a miniaturized sensor and are more suitable for the removal of oxygen in packings.

US 2012/0211372 A1 discloses systems and methods for enzymatic removal of oxygen from aqueous solutions. However, said systems and methods are not suitable for use in biosensors in which the content of an analyte is determined by means of oxidases.

DISCLOSURE OF THE INVENTION

It is therefore an object of the present invention to provide a method which removes dissolved oxygen from an aqueous solution and does not exhibit the above-described disadvantages of the prior art.

This object is achieved by a method as claimed in claim 1.

The method according to the invention uses an oxidase for oxygen removal.

The dissolved oxygen is removed via a coupled enzyme reaction using an oxidase and a catalase. In a first step, a first reaction is catalyzed by an oxidase, the first reaction involving reaction of oxygen with a substrate of the oxidase, for example a short-chain alcohol or formaldehyde, to form an aldehyde or an acid and hydrogen peroxide, and in a second step, the hydrogen peroxide is disproportionated to form water and ½ oxygen, catalyzed by a catalase for example, in a second reaction. The resultant oxygen is ultimately converted to water by cyclic passage through the first and the second step. The oxidase used is highly specific for oxygen as electron acceptor, and no transfer of electrons to mediators or other nonspecific molecules occurs (Azevedo, Biosensors & Bioelectronics, 2005). This particular property of the oxidase ensures that the removal of oxygen has no influence on the measurement results of enzyme-based biosensors, more precisely oxidase-based biosensors. The method described here removes the dissolved oxygen quickly and completely. By means of the coupled enzyme reaction, it is possible to effectively remove dissolved oxygen even from small sample volumes without direct reactions at the electrode of an electrochemical biosensor being able to occur to a more than negligible extent as a result of oxygen diffusion processes.

The method according to the invention is advantageously suitable for removing dissolved oxygen from aqueous solutions, especially for removing dissolved oxygen from aqueous solutions to improve the quality of results of electrochemical analyses which use oxidases as sensor enzyme specifically for the desired analyte, for example in the determination of glucose concentrations.

All components necessary for oxygen removal and determination of an analyte can be deposited as solid on the electrode of an electrochemical measurement cell. The enzymes used can be applied by drop-casting and subsequently dried. The substrate for the oxidase for oxygen removal—for example methanol, ethanol or propanol—can, for example, be processed by mixing with maltodextrin to form a water-soluble solid. Substrate in the context of the present invention encompasses especially reducing agent. Methanol can also be processed by addition of calcium acetate to form a water-soluble gel. Paraformaldehyde (CAS No: 30525-89-4), a further substrate for the oxidase for oxygen removal, is a solid which can likewise be used in an electrochemical measurement cell. The method according to the invention has the advantage that, by adding an aqueous sample containing the analyte, all necessary components are dissolved, meaning that labor-intensive sample preparation is not necessary. In addition, the use of solids advantageously improves the efficiency of the determination of the concentration of an analyte with the aid of an analyte-specific oxidase, since the solids have no influence on the oxidation reaction of the sensor enzyme and on the electrochemical processes of the measurement cell.

Furthermore, it is conceivable to use the method according to the invention in other chemical processes in which dissolved oxygen is an interfering factor, for example in the concentration analysis of phosphates or lactose with the aid of oxidase-based biosensors. The quality of the results of electrochemical analyses using oxygen-sensitive sensor enzymes, especially when the enzymes used are oxidases, is improved by the method according to the invention.

Advantageous embodiments and developments of the invention are apparent from the dependent claims and from the description with reference to the drawings.

According to a preferred embodiment of the present invention, the reducing agent used is a short-chain alcohol, preferably methanol or ethanol or propanol or butanol or pentanol, or formaldehyde or paraformaldehyde. It is conceivable to use the alcohol in a concentration of from 5 to 100 mmol/l, preferably from 45 mmol/l to 55 mmol/l. Paraformaldehyde can be used as a further possible substrate for the oxidase for oxygen removal. Paraformaldehyde is a polymer of formaldehyde and is present as a solid.

According to a further preferred embodiment of the present invention, the oxidase for oxygen removal that is used is an alcohol oxidase isolated from *Pichia* pastoris, *Candida boidinii, Hansenula* sp. or other organisms The stated oxidases advantageously improve the effect of the method according to the invention. Said oxidases have a high specific activity for short-chain alcohols and formaldehyde and are moreover inexpensively and commercially available. The intended oxidase is selected such that the enzymatic activity for the oxidation of an analyte is distinctly lower than for the oxidation of the reducing agent. The enzymatic activity for the oxidation of the analyte is, then, less than 5% of the enzymatic activity of the oxidation of the reducing agent.

According to a further preferred embodiment of the present invention, the disproportionation is achieved by means of catalysts, preferably by means of catalase, particularly preferably by means of catalase isolated from bovine liver. Catalase isolated from bovine liver advantageously improves the efficiency of the method according to the invention. Furthermore, said catalase is commercially available. However, it is also conceivable that *Aspergillus niger, Corynebacterium glutamicum* or *Micrococcus lysodeikticus* are used as catalase.

The present invention further provides a measurement system for electrochemical determination of an analyte in an aqueous solution in an electrochemical measurement cell, the measurement cell comprising electrodes and chemical reaction partners for carrying out a method according to the invention. The measurement system makes it possible to carry out electrochemical measurements, dissolved oxygen being removed using the method as claimed in any of claims 1 to 5 to improve the accuracy of measurement. In this case, dissolved oxygen is removed without the electrochemical determination with the aid of an oxidase being influenced by the process of oxygen removal.

According to a preferred embodiment of the present invention, wherein the chemical reaction partners are integrated in the measurement cell.

According to a preferred embodiment of the present invention, the electrodes are screen-printed electrodes. The production and use thereof is inexpensive and flexible. It is also conceivable to use glassy carbon electrodes as electrodes. The electrodes can be a few millimeters in size, preferably up to 3 mm in size.

According to a preferred embodiment of the present invention, the volume of the electrochemical measurement cell is ≤150 µl, preferably ≤100 µl. In a likewise preferred embodiment of the present invention, the volume can be in the range from ≥0.5 µl to ≥100 µl, preferably ≥0.5 µl to ≤50 µl, particularly preferably ≥0.5 µl to ≤10 µl.

According to a further preferred embodiment of the present invention, the measurement system comprises 1,1-ferrocenedimethanol as electron mediator. It is also conceivable that the sensor enzyme an enzyme of the oxidase class (EC number: 1.1.3) and comprises an electron mediator compatible with the sensor enzyme. Furthermore, it is conceivable that the electron mediator has a similar redox potential to the sensor enzyme. Furthermore, it is conceivable that further ferrocene derivatives are used as electron mediator. However, it is also conceivable to use other classes of electron mediators such as, for example, ferricyanides, conductive organic salts, redox hydrogels containing a complexed metal (e.g., iron or osmium or ruthenium), phenothiazines, phenoxazines or viologens. By using an oxidase from *P. pastoris*, it is possible to use the abovementioned electron mediators because this enzyme does not react therewith, but is specific for oxygen as electron acceptor.

According to a further preferred embodiment of the present invention, the measurement system comprises a redox polymer with an osmium complex as electron mediator.

According to a further preferred embodiment of the present invention, the analyte is glucose, lactose and/or phosphate, the sensor enzyme for oxidizing the analyte comprising glucose oxidase, lactose oxidase or a combination of xanthine oxidase and purine nucleoside phosphorylase. As a result, it is possible to measure the concentration of analyte, for example the glucose concentration, lactose concentration or phosphate concentration, of an aqueous solution. The oxidase in question, for example the glucose oxidase, is selected such that the enzymatic activity is distinctly lower for the oxidation of the reducing agent than for the oxidation of the analyte. The enzymatic activity for the oxidation of the reducing agent is, then, less than 5% of the enzymatic activity of the oxidation of the analyte.

According to a preferred embodiment of the invention, the transfer of electrons to the electron mediator, due to the oxidase for oxygen removal, causes is a measured current of ≤5% of the current that is measured in the case of the oxidation of the analyte. To ensure this, a specific concentration ratio between the oxidase for oxygen removal and the sensor enzyme must be determined.

It would however also be conceivable that the measurement system comprises lactose oxidase for determining lactose or a combination of xanthine oxidase and purine nucleoside phosphorylase for determining phosphate. Furthermore, it is however also conceivable that one embodiment of the present invention comprises an oxidase specific for an analyte not yet mentioned in the preceding embodiments.

The present invention further provides a method for electrochemical determination of a concentration of an analyte in an aqueous solution using a measurement system as claimed in any of claims 5 to 12, characterized in that dissolved oxygen in the aqueous solution is removed using a method as claimed in any of claims 1 to 5. The method makes it possible to determine the concentration of an analyte in an aqueous solution without dissolved oxygen present leading to undesired deviations of the measurement results.

According to a preferred embodiment of the present invention, the analyte is oxidized under catalysis by an oxidase in an oxidation reaction, electrons from the oxidation reaction being transported from an electron mediator to an electrode, the current arising as a result of the transport of the electrons through the electron mediator being measured. This makes it possible to determine the concentration of the analyte on the basis of a current between the electrodes of the measurement system used.

According to a further preferred embodiment of the present invention, the analyte is glucose, the oxidase used being glucose oxidase. What is hereby provided is a method for determining a glucose concentration in an aqueous solution without absorbed oxygen or the production of hydrogen peroxide leading to distorted results. It would however also be conceivable that the method uses lactose oxidase for determining lactose or a combination of xanthine oxidase and purine nucleoside phosphorylase for determining phosphate. Furthermore, it is however also conceivable that an oxidase specific for an analyte not yet mentioned in the preceding embodiments is used.

According to a further preferred embodiment of the present invention, the analyte is lactose or phosphate, the oxidase used being lactate oxidase or a combination of xanthine oxidase and purine nucleoside phosphorylase.

According to a further preferred embodiment of the present invention, the electron mediator used is 1,1-ferrocenedimethanol.

According to a further preferred embodiment of the present invention, the electron mediator used is a redox polymer with an osmium complex. It became apparent that 1,1-ferrocenedimethanol or a redox hydrogel with complexed osmium as electron mediator increases the quality of the measurement results of the method. It is also conceivable that other classes of electron mediators, such as, for example, ferricyanides, conductive organic salts, metal complexes (e.g., iron or osmium or ruthenium complexes), phenothiazines, phenoxazines or viologens, are used.

Further details, features and advantages of the invention are revealed by the drawings and by the following description of preferred embodiments with reference to the drawings. At the same time, the drawings merely illustrate exemplary embodiments of the invention that do not restrict the essential concept of the invention.

EXEMPLARY EMBODIMENT OF THE INVENTION

Figure 1:
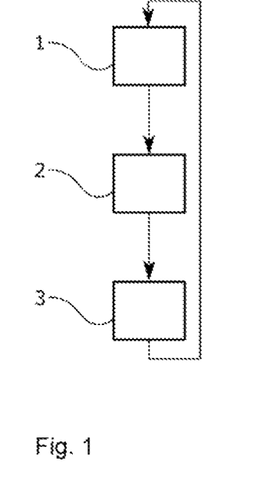
FIG. 1 show the basic principle of the method for removing dissolved oxygen according to one exemplary embodiment of the present invention.

FIG. 1 schematically represents the basic principle of the method for removing dissolved oxygen 12 according to one exemplary embodiment of the present invention as a flow chart. In the first step 1, a reducing agent 15, in this case methanol, reacts with oxygen 12 to form an aldehyde 16 and hydrogen peroxide 13. An oxidase for oxygen removal 14, in this case alcohol oxidase, serves as catalyst of this reaction. In the second step 2, the hydrogen peroxide 13 is reduced to form water 18 and the catalase 17 is oxidized. Furthermore, the oxidized catalase 17 and additionally hydrogen peroxide 13 are reduced to form water 18 and oxygen 12. The overall equation of the second step 2 is $2H_2O_2 \rightarrow O_2 + 2H_2O$. After the first step 1 and the second step 2 have been passed through, 1 $O_2$ has decreased to ½ $O_2$. By passing through the first step 1 and the second step 2 multiple times, the dissolved oxygen 12 is thus removed.

Figure 2:
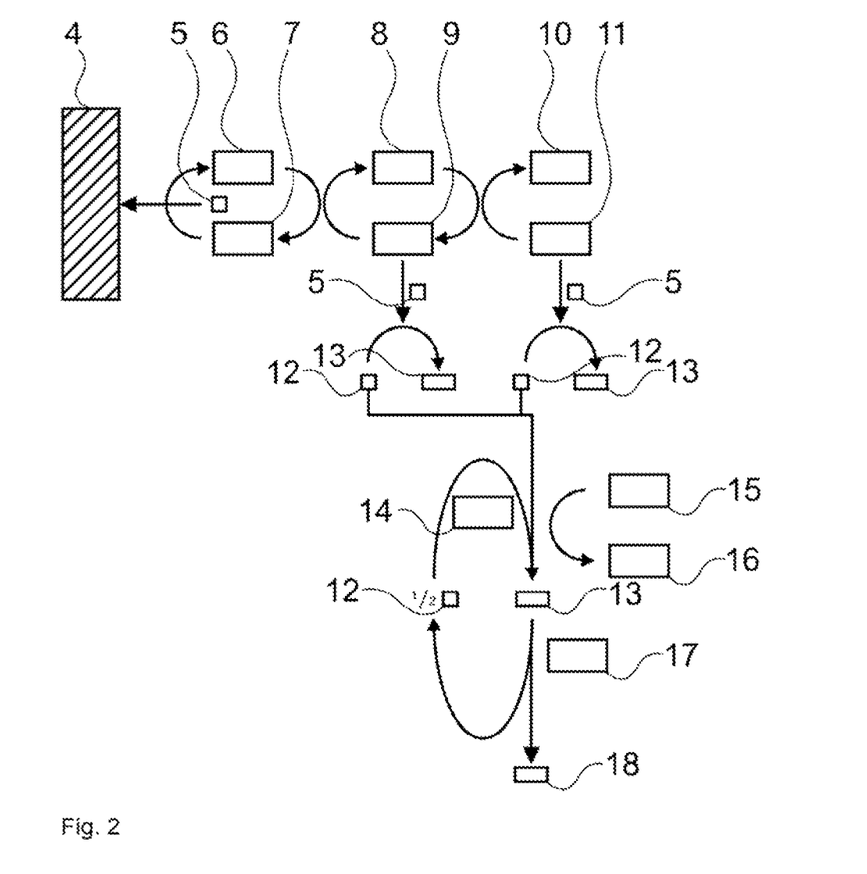
FIG. 2 shows the functional principle of the electrochemical biosensor for determining the concentration of the analyte of the aqueous sample, in which dissolved oxygen is removed according to one exemplary embodiment of the present invention.

FIG. 2 schematically represents the basic principle of the method for removing dissolved oxygen 12 according to one exemplary of the present invention as a flow chart.

In the first step 1 of the method, the electrode 4 takes up an electron 5 and converts the reduced mediator 7 into the oxidized form. The oxidized sensor enzyme 8 (e.g., glucose oxidase) oxidizes the analyte 11 (e.g., glucose) and is, in doing so, reduced to the reduced sensor enzyme 9. If the analyte 11 is glucose, gluconolactone is formed as oxidized analyte 10.

As a side-reaction, the reduced sensor enzyme 9 can be oxidized by dissolved oxygen 12 with release of an electron 5. At the same time, hydrogen peroxide 13 is released, which causes interference at the electrode 4.

The method according to the invention can completely remove the dissolved oxygen 12. This involves reaction of the reducing agent 15, in this case an alcohol, with the oxygen 12 to form the aldehyde 16 and hydrogen peroxide 13. In various alternative embodiments, the reducing agent 15 can be ethanol, propanol, butanol, pentanol and, preferably, methanol. An oxidase for oxygen removal 14, in this case alcohol oxidase, serves as catalyst of this reaction. The oxidase for oxygen removal 14 that is used is highly selective for oxygen 12 and does not use artificial electron mediators for transfer of electrons 5. This property makes it possible to remove oxygen 12 in oxidase-based biosensors without interfering therewith. In the second step 2, the hydrogen peroxide 13 is reduced to form water 18 and the catalase 17 is oxidized. Furthermore, the oxidized catalase 17 and the hydrogen peroxide 13 are reduced to form water 18 and ½ oxygen 12. After the first step 1 and the second step 2 have been passed through, 1 oxygen 12 has decreased to ½ oxygen 12. By cyclically passing through the first step 1 and the second step 2 multiple times, the dissolved oxygen 12 is thus completely removed.

Figure 3:
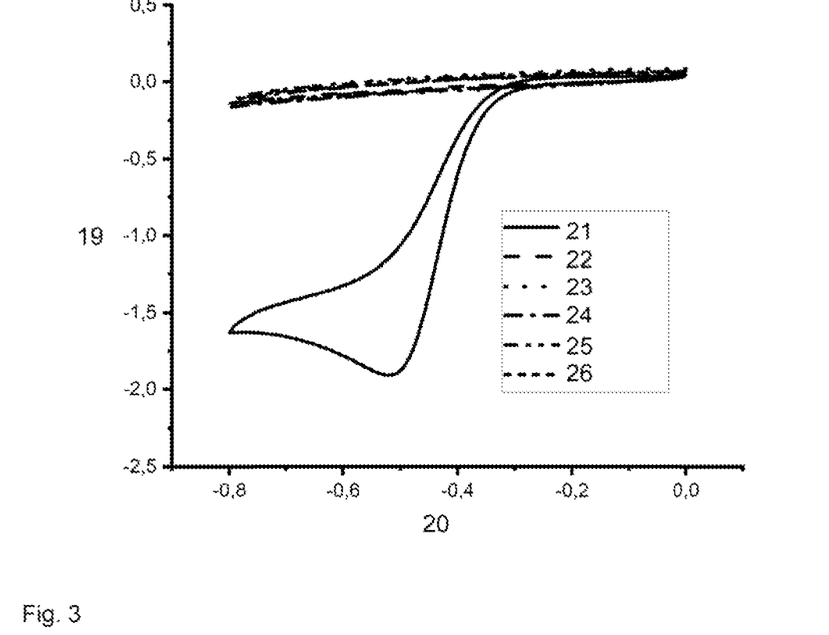
FIG. 3 shows the electrochemical characterization of various short-chain alcohols as reducing agent for the oxidase for oxygen removal.
Figure 4:
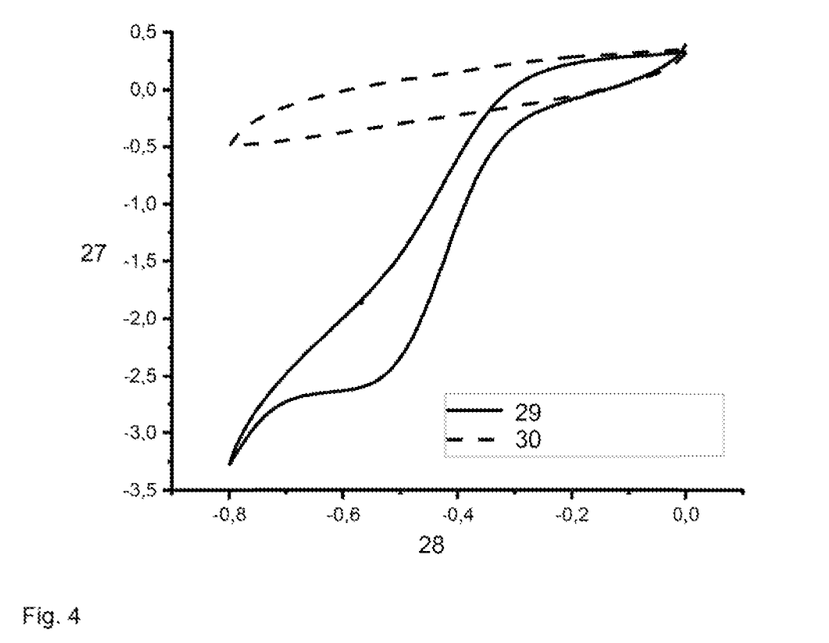
FIG. 4 shows the electrochemical characterization of maltodextrin-methanol solid as reducing agent for the oxidase for oxygen removal.

The oxidase for oxygen removal 14 oxidizes a substrate and removes dissolved oxygen 12 in doing so. FIG. 3 shows the removal of oxygen 12 with the aid of various substrates. According to one exemplary embodiment of the present invention, methanol or ethanol or propanol or butanol or pentanol can be used as substrate with a concentration of 50 mmol/l. According to a preferred embodiment, the alcohol is provided in solid form. FIG. 4 shows the removal of oxygen 12 with the reducing agent 15 methanol absorbed in maltodextrin. To this end, the reducing agent 15 is added to maltodextrin until the powder can no longer absorb liquid. The methanol excess is removed by evaporation. The reducing agent-maltodextrin absorbed for the method preferably contains approximately 5 percent by weight of methanol. The solid is added to the reaction mixture before the start of the reaction (1 mg to 100 μl). In this case, the oxygen 12 is removed just as effectively as by the addition of a liquid substrate (cf. FIG. 3).

Figure 5:
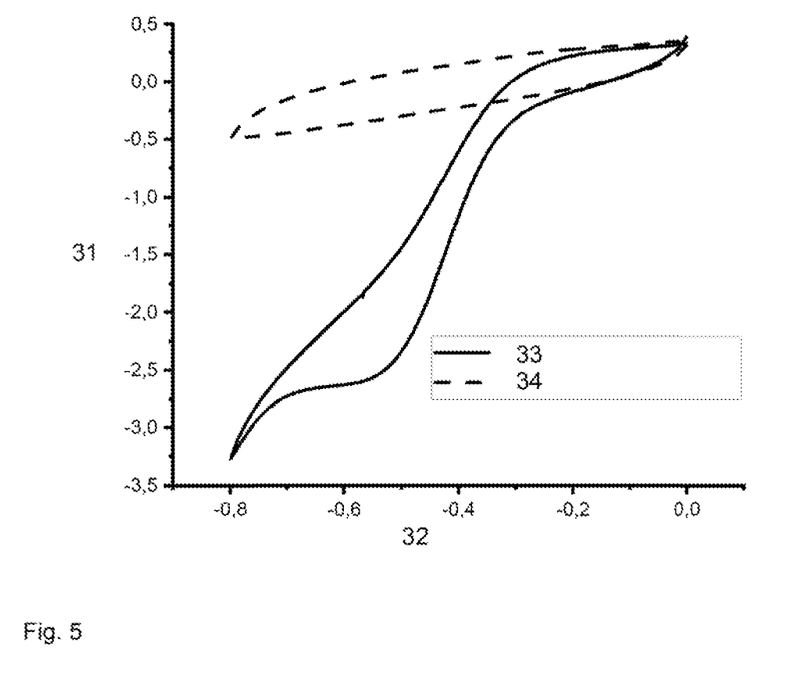
FIG. 5 shows the electrochemical characterization of calcium acetate-methanol solid as reducing agent for the oxidase for oxygen removal.

FIG. 5 shows the removal of oxygen 12 with the reducing agent 15 methanol absorbed in calcium acetate. To this end, a saturated solution of calcium acetate is prepared (3 g of $Ca(CH_3COO)_2$ to 10 g of water). Thereafter, 40 ml of methanol is added under stirring. Thereafter, 2 mg of this solid is added to 100 μl of reaction mixture. In this case, the oxygen 12 is removed just as effectively as by the addition of liquid substrate.

Figure 6:
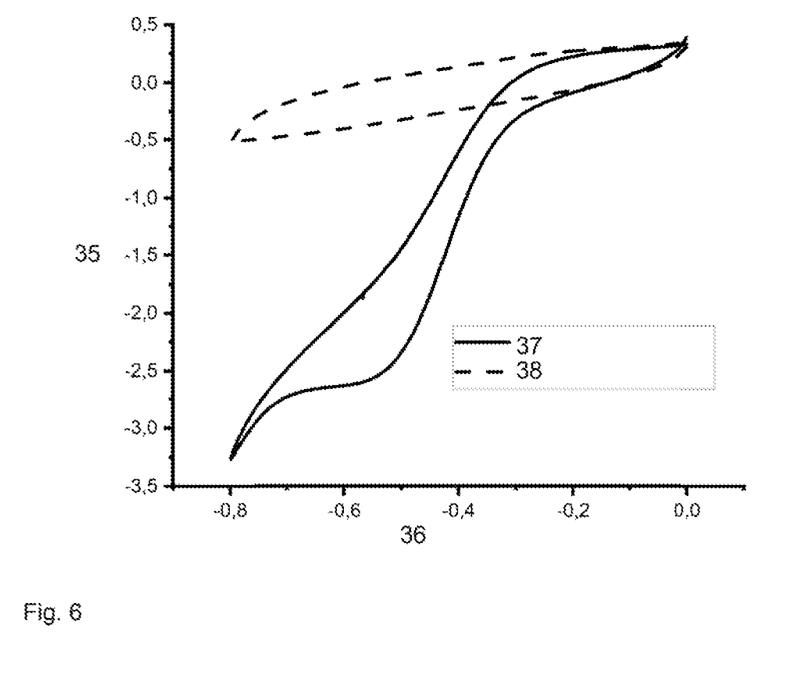
FIG. 6 shows the electrochemical characterization of paraformaldehyde as reducing agent for the oxidase for oxygen removal.

In a further exemplary embodiment of the present invention, paraformaldehyde, a polymer of formaldehyde, is used as solid reducing agent 15 for oxygen removal. To this end, 1 mg of paraformaldehyde is added to 100 μl of reaction mixture. FIG. 6 shows the electrochemical characterization of oxygen removal. The oxygen 12 is removed just as effectively as by the addition of liquid substrate.

Figure 7:
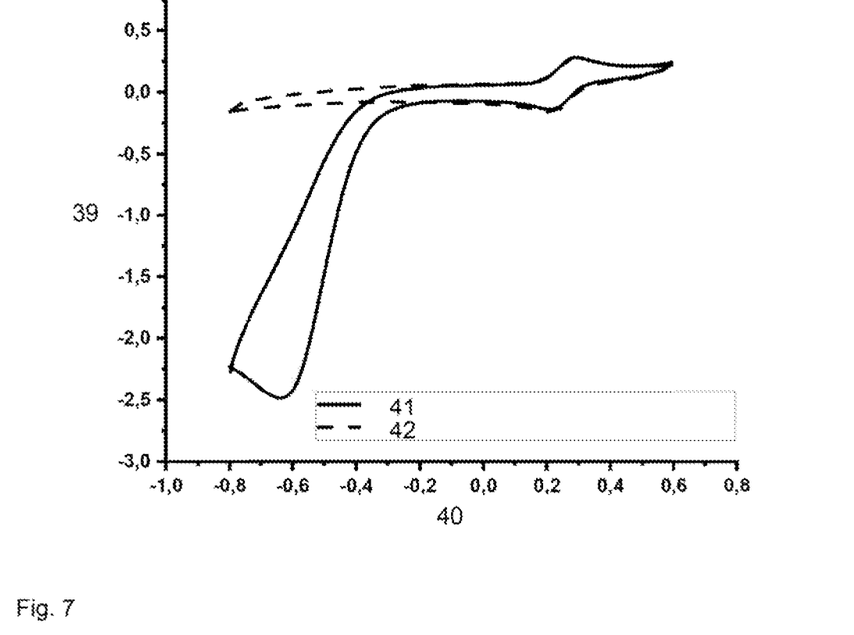
FIG. 7 shows the electrochemical characterization of the electron mediator 1,1-ferrocenedimethanol together with the oxidase for oxygen removal.

The oxidase for oxygen removal 14 is not capable of transferring electrons 5 to an electron mediator. The graph shown in FIG. 7 contains experimental data of an experiment in which the influence on oxygen removal of the oxidase was tested. Said experiment showed that the oxidase for oxygen removal 14 does not transfer electrons 5 to the electron mediator 1,1-ferrocenedimethanol, but can continue to remove the oxygen 12 from the solution.

Figure 8:
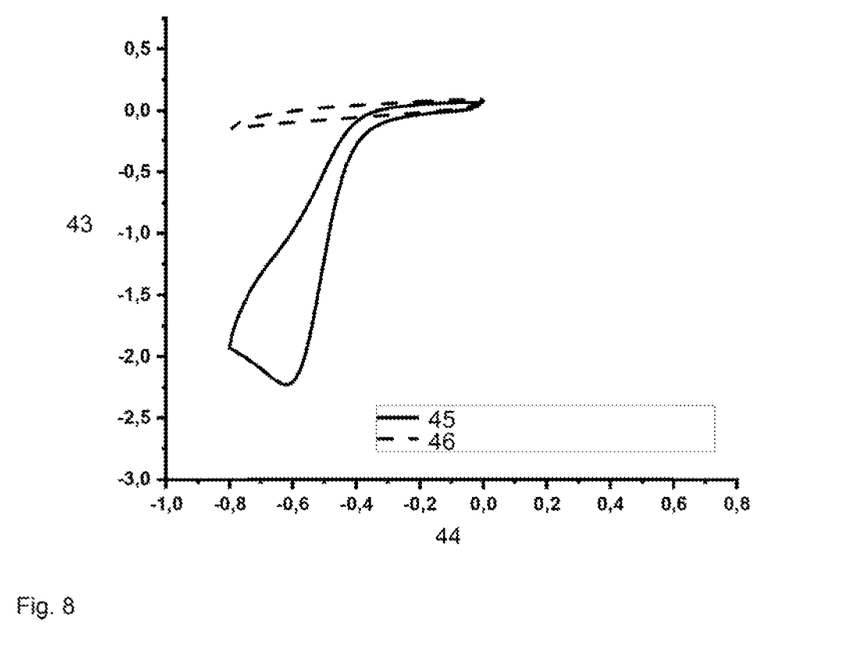
FIG. 8 shows the electrochemical characterization of the oxidase for oxygen removal with the electron mediator 1,1-ferrocenedimethanol in solution. The oxidase cannot transfer electrons to this mediator.

The oxidase for oxygen removal 14 is not capable of oxidizing the analyte 11. FIG. 8 shows a graph containing data from an experiment in which glucose is added as substrate of a biosensor according to the invention. The oxidase for oxygen removal 14 is capable of completely removing the oxygen 12 from the solution. The glucose added shows no influence on the background current of a control experiment (cf. FIG. 3).

Figure 9:
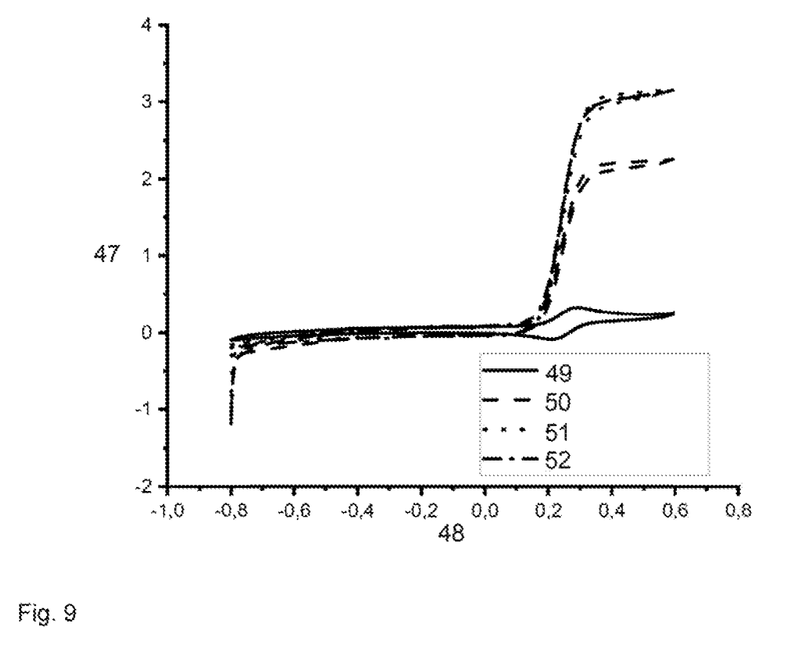
FIG. 9 shows the electrochemical characterization of the oxidase for oxygen removal with glucose in solution. The oxidase for oxygen removal cannot oxidize glucose.
Figure 10:
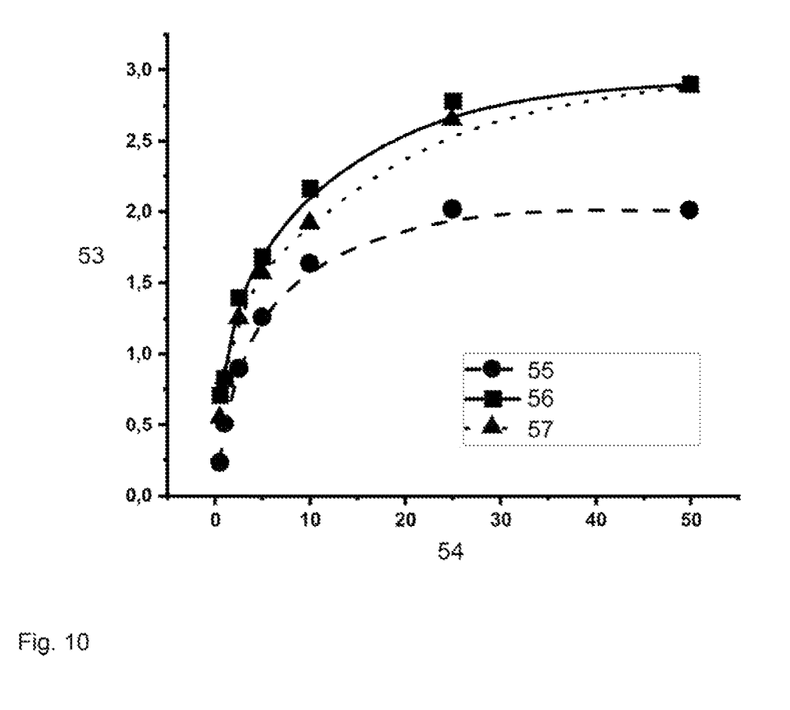
FIG. 10 shows the determination of a range of concentrations of glucose under various conditions in a sample volume of 1000 µl.

To demonstrate the usability of the oxidase for oxygen removal 14 in a biosensor system, a biosensor for glucose is tested under various conditions. The data of this series of tests are depicted in FIG. 9 in graph form. The current for the oxidation of the analyte 11 glucose by the sensor enzyme was tested under an air atmosphere, an argon atmosphere and under a room-air atmosphere in combination with the oxidase for oxygen removal 14 at a glucose concentration of 50 mmol/l. From the comparison of these measurements, it can be seen that the measured current under an argon atmosphere is identical to the current which was measured when the oxidase for oxygen removal was used under a room-air atmosphere. In comparison, the measured current is lower when the oxidase for oxygen removal 14 is not present in the system. FIG. 10 depicts a range of concentrations of a glucose biosensor. The presence of oxygen 12 in the solution leads to up to 30% lower measured currents, since the sensor enzyme transfers electrons 5 to the oxygen 12 present in the solution.

Figure 11:
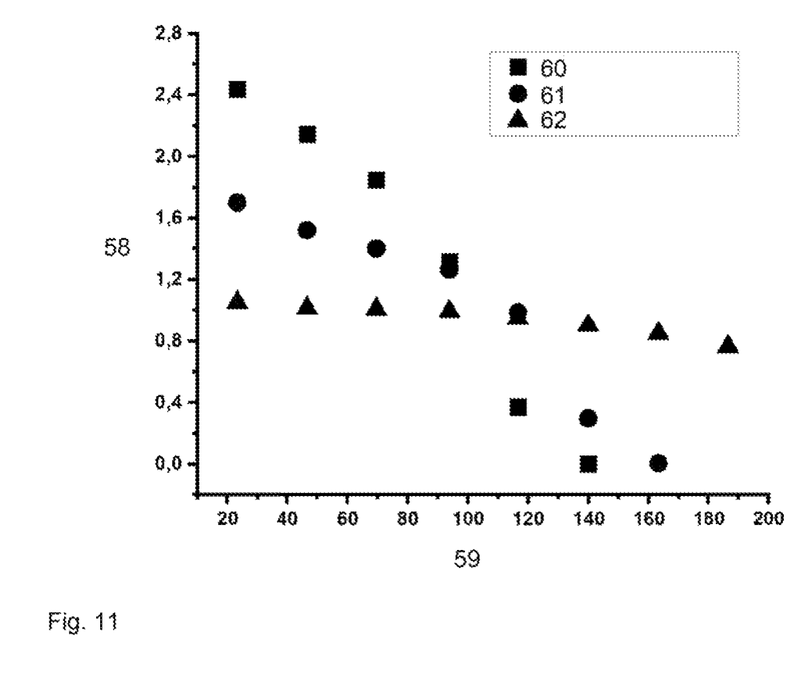
FIG. 11 shows the influence of various concentration ratios of the oxidase for oxygen removal and the sensor enzyme.

A preferred ratio between the sensor enzyme and the oxidase for oxygen removal 14 is 1:10. FIG. 11 depicts the experimental demonstration of this optimization. This can be shown by a constant current over a measurement time of 200 minutes. The constant current indicates that oxygen 12 which dissolves from air into the solution can be immediately and completely removed.

Figure 12:
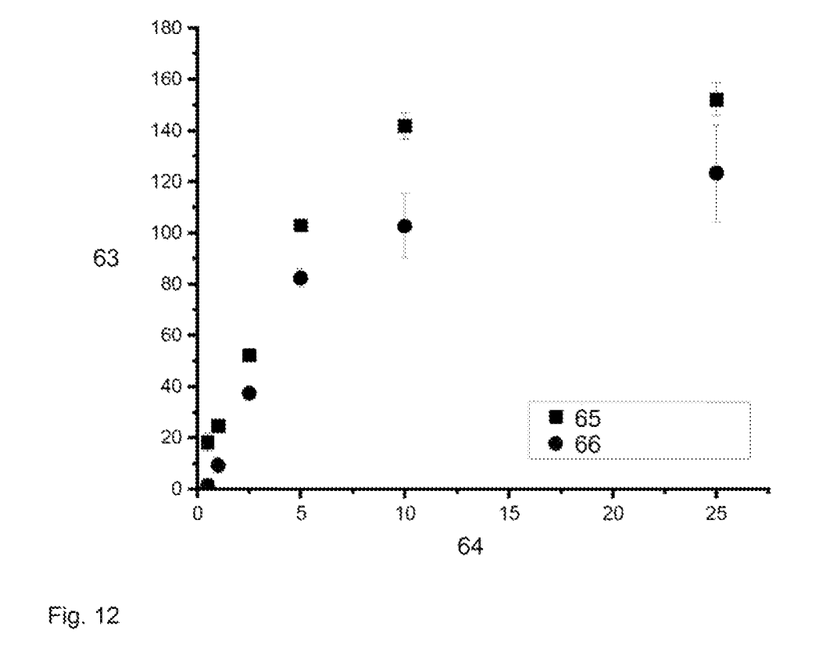
FIG. 12 shows the determination of a range of concentrations of glucose under various conditions in a sample volume of 100 µl.

FIG. 12 shows the detection of a range of concentrations of glucose in a reaction volume of 100 μl by an oxygen-insensitive biosensor. The interference by oxygen 12 in the solution leads to the measured current being on average 25% and maximally 90% (~10 mmol/l glucose concentration) lower.

LIST OF REFERENCE SIGNS

FIG. 1
1 First step
2 Second step
3 Third step
FIG. 2
4 Electrode 5 Electron
6 Oxidized mediator
7 Reduced mediator
8 Oxidized sensor enzyme
9 Reduced sensor enzyme
10 Oxidized analyte
11 Analyte
12 Oxygen
13 Hydrogen peroxide
14 Oxidase for oxygen removal
15 Reducing agent
16 Aldehyde
17 Catalase
18 Water
FIG. 3
19 Y-axis: Current in μA
20 X-axis: Potential in V (E vs Ag/AgCl 3M KCl)
21 Control in phosphate buffer (100 mM, pH 7.0-7.5)
22 1 ml of phosphate buffer+50 mmol/l methanol
23 1 ml of phosphate buffer+50 mmol/l ethanol
24 1 ml of phosphate buffer+50 mmol/l propanol
25 1 ml of phosphate buffer+50 mmol/l butanol
26 1 ml of phosphate buffer+50 mmol/l pentanol
FIG. 4
27 Y-axis: Current in μA
28 X-axis: Potential in V (E vs Ag/AgCl 3M KCl)
29 Control in 1 ml of phosphate buffer (100 mM, pH 7.0-7.5)
30 1 ml of phosphate buffer+maltodextrin-methanol solid
FIG. 5
31 Y-axis: Current in μA
32 X-axis: Potential in V (E vs Ag/AgCl 3M KCl)
33 Control in 1 ml of phosphate buffer (100 mM, pH 7.0-7.5)
34 1 ml of phosphate buffer+calcium acetate-methanol solid
FIG. 6
35 Y-axis: Current in μA
36 X-axis: Potential in V (E vs Ag/AgCl 3M KCl)
37 Control in 1 ml of phosphate buffer (100 mM, pH 7.0-7.5)
38 1 ml of phosphate buffer+paraformaldehyde (0.1 mg/ml)
FIG. 7
39 Y-axis: Current in μA
40 X-axis: Potential in V (E vs Ag/AgCl 3M KCl)
41 1 ml of phosphate buffer (100 mM, pH 7.0-7.5), 10 U AOX, 2000 U CAT, 100 μmol/l 1,1-ferrocenedimethanol
42 1 ml of phosphate buffer (100 mM, pH 7.0-7.5), 10 U AOX, 2000 U CAT, 100 μmol/l 1,1-ferrocenedimethanol, 50 mmol/l ethanol
FIG. 8
43 Y-axis: Current in μA
44 X-axis: Potential in V (E vs Ag/AgCl 3M KCl)
45 1 ml of phosphate buffer (100 mM, pH 7.0-7.5), 10 U AOX, 2000 U CAT, 50 mmol/l glucose
46 1 ml of phosphate buffer (100 mM, pH 7.0-7.5), 10 U AOX, 2000 U CAT, 50 mmol/l glucose, 50 mmol/l ethanol
FIG. 9
47 Y-axis: Current in μA
48 X-axis: Potential in V (E vs Ag/AgCl 3M KCl)
49 Control without glucose: 1 ml of phosphate buffer (100 mM, pH 7.0-7.5), 10 U AOX, 2000 U CAT, 15 U GOX, 100 μmol/l 1,1-ferrocenedimethanol, 50 mmol/l ethanol
50 Glucose determination, air atmosphere: 1 ml of phosphate buffer (100 mM, pH 7.0-7.5), 15 U GOX, 100 μmol/l 1,1-ferrocenedimethanol, 50 mmol/l glucose
51 Glucose determination with oxygen removal, air atmosphere: 1 ml of phosphate buffer (100 mM, pH 7.0-7.5), 10 U AOX, 2000 U CAT, 15 U GOX, 100 μmol/l 1,1-ferrocenedimethanol, 50 mmol/l ethanol, 50 mmol/l glucose
52 Glucose determination, argon atmosphere: 1 ml of phosphate buffer (100 mM, pH 7.0-7.5), 15 U GOX, 100 μmol/l 1,1-ferrocenedimethanol, 50 mmol/l glucose
FIG. 10
53 Y-axis: Current in μA
54 X-axis: Glucose concentration in mmol/l
55 Control, air atmosphere: 1 ml of phosphate buffer (100 mM, pH 7.0-7.5), 15 U GOX, 100 μmol/l 1,1-ferrocenedimethanol
56 Glucose determination with oxygen removal, air atmosphere: 1 ml of phosphate buffer (100 mM, pH 7.0-7.5), 10 U AOX, 2000 U CAT, 15 U GOX, 100 μmol/l 1,1-ferrocenedimethanol, 50 mmol/l ethanol57 Glucose determination, argon atmosphere: 1 ml of phosphate buffer (100 mM, pH 7.0-7.5), 15 U GOX, 100 μmol/l 1,1-ferrocenedimethanol
FIG. 11
58 Y-axis: Current in μA
59 X-axis: Time in minutes
60 Glucose determination with oxygen removal, air atmosphere: 1 ml of phosphate buffer (100 mM, pH 7.0-7.5), 10 U AOX, 2000 U CAT, 15 U GOX, 100 μmol/l 1,1-ferrocenedimethanol, 100 mmol/l ethanol
61 Glucose determination with oxygen removal, air atmosphere: 1 ml of phosphate buffer (100 mM, pH 7.0-7.5), 20 U AOX, 2000 U CAT, 10 U GOX, 100 μmol/l 1,1-ferrocenedimethanol, 100 mmol/l ethanol
62 Glucose determination with oxygen removal, air atmosphere: 1 ml of phosphate buffer (100 mM, pH 7.0-7.5), 50 U AOX, 2000 U CAT, 5 U GOX, 100 μmol/l 1,1-ferrocenedimethanol, 100 mmol/l ethanol
FIG. 12
63 Y-axis: Current in μA
64 X-axis: Glucose concentration in mmol/l
65 Glucose determination with oxygen removal, air atmosphere: 1 ml of phosphate buffer (100 mM, pH 7.0-7.5), 10 U AOX, 2000 U CAT, 15 U GOX, 100 μmol/l 1,1-ferrocenedimethanol, 100 mmol/l ethanol
66 Glucose determination with oxygen removal, argon atmosphere: 1 ml of phosphate buffer (100 mM, pH 7.0-7.5), 2000 U CAT, 10 U GOX, 100 μmol/l 1,1-ferrocenedimethanol

What is claimed is:

1. A method for removing dissolved oxygen in an electrochemical biosensor which uses a first oxidase for oxygen removal and uses a second oxidase as sensor enzyme, wherein
   i) in a first step, a first reaction is catalyzed by the first oxidase for oxygen removal, the first reaction involving reaction of oxygen with a reducing agent to form hydrogen peroxide without electrons being transferred to an acceptor other than oxygen, wherein the only component of the electrochemical biosensor oxidized in the first reaction is the reducing agent,
   ii) in a second step, the hydrogen peroxide is disproportionated to form water in a second reaction,
   iii) in a third step, the second oxidase serving as sensor enzyme catalyzes the oxidation of an analyte of an aqueous solution of the electrochemical biosensor in a third reaction, the oxidase serving as sensor enzyme being specific for the analyte, the electrons released by the oxidation of the analyte being transferred solely to an electron mediator;

optionally, wherein the only component of the aqueous solution oxidized in the third step is the analyte.

2. The method as claimed in claim 1, wherein the reducing agent used is a short-chain alcohol.

3. The method of claim 2, wherein the short-chained alcohol is methanol, ethanol, propanol, butanol, pentanol, formaldehyde, or paraformaldehyde.

4. The method as claimed in claim 1, wherein the first oxidase for oxygen removal that is used is an oxidase isolated from *Pichia pastoris* or *Candida boidinii* or *Hansenula* sp.

5. The method as claimed in claim 1, wherein the disproportionation of hydrogen peroxide to form water is achieved by means of one or more catalysts, optionally by means of a catalase.

6. The method as claimed in claim 5, wherein the catalyst used is the catalase and is a catalase isolated from bovine liver.

7. The method of claim 1, wherein the method comprises determining a concentration of the analyte in the aqueous solution.

8. A measurement system for electrochemical determination of an analyte in an aqueous solution in an electrochemical measurement cell, the measurement cell comprising electrodes, the measurement cell comprising a first oxidase for oxygen removal and a second oxidase for sensing the analyte;

wherein the first oxidase is capable of catalyzing oxygen removal in a first reaction involving reaction of the oxygen with a reducing agent to form hydrogen peroxide, wherein the only component of the electrochemical biosensor that is oxidized in the first reaction step is the reducing agent;

wherein the measurement cell comprises a reaction component for disproportionation of the hydrogen peroxide in a second reaction;

wherein the second oxidase is capable of catalyzing the oxidation of the analyte in an aqueous solution in a third reaction, wherein the second oxidase is specific for the analyte;

wherein the measurement cell includes an electron mediator, wherein electrons released by the oxidation of the analyte are transferred solely to the electron mediator.

9. The measurement system as claimed in claim 8, wherein the first oxidase, the second oxidase, the reaction component, the reducing agent, and the electron mediator, are integrated in the measurement cell.

10. The measurement system as claimed in claim 8, wherein the electrodes are screen-printed electrodes.

11. The measurement system as claimed in claim 8, wherein a volume of the measurement cell is smaller than ≤150 µl, optionally ≤100 µl.

12. The measurement system as claimed in claim 8, wherein the measurement system comprises 1,1-ferrocenedimethanol as electron mediator.

13. The measurement system as claimed in claim 8, wherein the measurement system comprises a redox polymer with an osmium complex as electron mediator.

14. The measurement system as claimed in claim 8, wherein the analyte is glucose, lactose and/or phosphate, a sensor enzyme for oxidizing the analyte comprising glucose oxidase, lactose oxidase or a combination of xanthine oxidase and purine nucleoside phosphorylase.

15. A method comprising a step of electrochemically determining a concentration of an analyte in an aqueous solution using the measurement system as claimed in claim 8.

16. The method as claimed in claim 15, wherein the analyte is oxidized under catalysis by the second oxidase in an oxidation reaction, electrons from the oxidation reaction being transported from the electron mediator to an electrode, wherein the step of determining the concentration of the analyte includes a step of measuring a current arising as a result of the transport of the electrons through the electron mediator.

17. The method as claimed in claim 15, wherein the analyte is glucose, and the second oxidase is glucose oxidase.

18. The method as claimed in claim 15, wherein the analyte is lactose or phosphate, and the second oxidase is lactate oxidase or a combination of xanthine oxidase and purine nucleoside phosphorylase.

19. The method as claimed in claim 15, wherein the electron mediator used is 1,1-ferrocenedimethanol.

20. The method as claimed in claim 15, wherein the electron mediator used is a redox polymer with an osmium complex.

* * * * *